United States Patent [19]

Ruetman et al.

[11] 3,962,260
[45] June 8, 1976

[54] 6-HYDRAZINO-2,3,5-TRIHALO-4-ALKYLTHIO PYRIDINES AND METHOD OF PREPARING SAME

[75] Inventors: Sven H. Ruetman, Walnut Creek; Richard N. Watson, Antioch, both of Calif.

[73] Assignee: The Dow Chemical Company, Midland, Mich.

[22] Filed: July 31, 1975

[21] Appl. No.: 600,674

Related U.S. Application Data

[62] Division of Ser. No. 536,790, Dec. 27, 1974.

[52] U.S. Cl. .................. 260/294.8 F; 260/294.8 G; 424/263
[51] Int. Cl.² ........................................ C07D 213/62
[58] Field of Search ............... 260/294.8 F, 294.8 G

[56] References Cited
UNITED STATES PATENTS

| | | | |
|---|---|---|---|
| 3,296,272 | 1/1967 | Johnston | 260/294.8 F |
| 3,475,441 | 10/1969 | Levine | 260/294.8 F |

OTHER PUBLICATIONS

Klingsberg, Pyridine and its Derivatives, Part 2, Interscience Pub. pp. 488–490, 501 (1961).

Primary Examiner—Alan L. Rotman
Attorney, Agent, or Firm—Robert R. Stringham

[57] ABSTRACT

Novel compounds having the formula

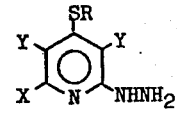

wherein R is an alkyl group of 1 to 5 carbons, X is Br or Cl and Y is Cl or is Br except when X is Cl, are prepared by the reaction of a hydrazine source material with a corresponding compound of the formula

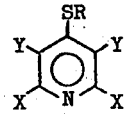

The product compounds are fungicidal in their own right and are readily oxidized to highly active trihalo-4-alkylsulfonyl pyridine fungicides.

6 Claims, No Drawings

6-HYDRAZINO-2,3,5-TRIHALO-4-ALKYLTHIO PYRIDINES AND METHOD OF PREPARING SAME

CROSS-REFERENCE TO RELATED APPLICATION

This is a division of application Ser. No. 536,790 filed Dec. 27, 1974.

BACKGROUND OF THE INVENTION

Compounds of the formula

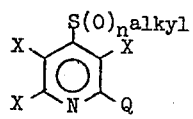

wherein $n = 1$ or 2, Q is H or X and X is Br or Cl are taught in U.S. Pat. No. 3,296,272 to be highly active fungicides. Among such compounds is included the commercial paint film preservative and industrial fungicide, DOWICIL-A-40, having the formula

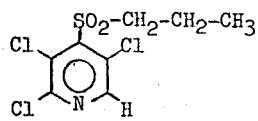

U.S. Pat. No. 3,415,832 describes and claims the preparation of the preceding compound (and other such compounds) by oxidation of the corresponding alkylthio (sulfide) compounds with chlorine water. The precursor sulfide compounds are prepared by replacement of a 4-halo substituent in a corresponding polyhalopyridine with an —S alkyl group. For example, the 4-propylthio precursor to DOWICIL-A-40, has been made from 2,3,4,5-tetrachloro pyridine, as taught in U.S. Pat. No. 3,364,223.

Several methods are known for the production of the latter compound and for other tetrahalopyridines but experience has shown that each of said methods leaves something to be desired as a commercial process. It has become apparent that a method based directly on less expensive and more readily obtained starting materials, such as perhalopyridines, would be advantageous. Such a method requires selective replacement of a halogen substituent in the 2 (or 6) position by a hydrogen at some stage of the synthesis.

It is known (I. Collins et al, J. Chem. Soc., (c); pp. 167–174 (1971)) that halogens ortho and para to the ring nitrogen in pentahalopyridines are reactive with hydrazine hydrate. Collins et al also reported the formation of 2,3,4,5-tetrachloropyridine when pentachloropyridine-1-oxide is reacted with hydrazine hydrate and attribute this to intra-molecular deoxidation/decomposition of an intermediate product, tetrachloro-6-hydrazinopyridine-1-oxide. However, halogens in the 4-position of perhalopyridines are several fold more reactive with hydrazine than halogens in the 2- (or 6) positions, thus indicating replacement of the 4-halogen with alkylthio before introduction of a hydrazino moiety ortho to the ring nitrogen. A difficulty with this, however, is the well known ease of displacement of alkylthio substituents from aromatic rings by hydrazine. Further, the 4-position in polyhalopyridines is activated to nucleophilic attack by the effect of the halogens present.

SUMMARY OF THE INVENTION

It has now been discovered that certain 2,3,5,6-tetrahalo-4-(alkylthio) pyridines can be converted in good yields to corresponding 6-hydrazino-2,3,5-trihalo-4-(alkylthio) pyridines with only very minor concomitant-S-alkyl losses. The resulting hydrazino compounds are novel and are active as such against a variety of microbial organisms. The hydrazino group may be readily removed and the resulting sulfide compound then oxidized by known methods to the corresponding sulfoxide or sulfone fungicides. Removal of the hydrazino group (replacement by —H) is followed by in-situ oxidation of the sulfide group, in a preferred use of the hydrazino compounds.

More precisely, the novel compounds of the present invention are 6-hydrazino-2,3,5-trihalo-4-(alkylthio) pyridines of the formula

wherein R is an alkyl group of from 1 to 5 carbons, X is Cl or Br and Y is the same in each occurrence and is Cl or is Br except when X is Cl.

The method of the present invention is a process for preparing compounds of the preceding formula, said process comprising reacting a tetrahalo 4-(alkylthio) pyridine of the formula

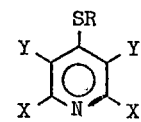

wherein R, X and Y are as above defined, with hydrazine and thereby effecting replacement of an X- group in said tetrahalo-4-(alkylthio) pyridine by a hydrazino moiety.

In a narrower aspect, the method of the present invention comprises carrying out the preceding reaction as the first step in a two-step sequence for the preparation of a corresponding 2,3,5-trihalo-4-(alkylthio) pyridine of the formula

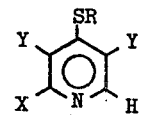

the second step in said sequence comprising reacting the hydrazino compound produced in said first step with an oxidant to effect replacement of the hydrazino moiety therein by a hydrogen. The oxidation preferably is carried out under basic conditions.

In a preferred aspect, the present method comprises carrying out said oxidation step by reaction of the hydrazino compound with hypochlorite or hypobromite ion under basic conditions.

DETAILED DESCRIPTION OF THE INVENTION

I. Preparation of the hydrazino compounds of the invention.

The tetrahalo-4-alkylthio compounds which may be employed in the preparation of the novel hydrazino compounds of the invention are:

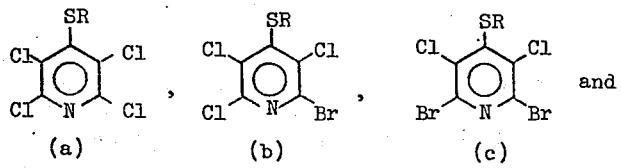 and 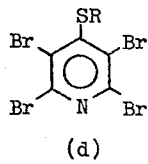

wherein R is a branched or straight chain alkyl group of 1 to 5 carbons. In compounds of type (b), replacement of the alpha-bromine with a hydrazino moiety will be favored over replacement of the alpha-chlorine.

Methods which may be employed to prepare these compounds are disclosed in U.S. Pat. No. 3,364,223, cited earlier herein. Pentachloropyridine, a convenient precursor to compounds of formulas (a) through (c), is readily made by the vapor phase chlorination of pyridine, as disclosed in U.S. Pat. No. 3,420,833. Pentabromopyridine, the precursor to compounds of formula (d), may be prepared by vapor phase bromination of pyridine, in the manner disclosed in U.S. Pat. No. 3,595,868 for perbromination of cyanopyridines.

HYDRAZINE SOURCE MATERIALS

Suitable hydrazine source materials for the foregoing reaction with a tetrahalo-4-(alkylthio)-pyridine are anhydrous hydrazine, hydrazine hydrate and acid salts from which hydrazino may be liberated in situ by a stronger base, such as, for example, hydrazine formate, hydrazine mono- or dihydrochloride, hydrazine sulfate, dihydrazine sulfate, etc. Hydrazine hydrate is preferred as being commercially available and as being readily soluble in the preferred media (polar solvents) for the reaction.

REACTION MEDIA

The reaction between hydrazine and the tetrahalo-4-(alkylthio) pyridine can be carried out neat. However, numerous by-products form and the hydrazino product tends to be oxidized in situ by any excess of hydrazine present, particularly at higher temperatures. Accordingly, this is a less preferred mode of operation.

In another option, a non-polar organic solvent may be employed as the medium for the reaction, either or both of the reactants being dissolved or suspended (as by stirring, for example) therein. This also is a less suitable alternative.

The preferred media are polar organic liquids, such as alcohols, dimethyl sulfoxide (DMSO), sulfolane and dimethyl formamide (DMF), for example. Preferably, such solvents are anhydrous but limited amounts of water may be present. Water contents in excess of about 20 wt. percent result in considerably reduced reaction rates.

The most preferred media are alcohols of from 1 to 3 carbons, methanol being particularly preferred.

It is essential that any medium employed be not detrimentally reactive. Preferably, the medium used will be inert, i.e., will be recoverable from the reaction mixture unaltered.

REACTION TEMPERATURES

The reaction with hydrazine is relatively slow and elevated temperatures, such as from about 80° to about 100°, are preferred. However, the reaction proceeds at temperatures down to about 45°, the melting point of tetrachloro-4-propylthiopyridine. Loss of the alkylthio group is more noticeable at higher temperatures, such as about 120°, and may become excessive at temperatures above about 150°. Temperatures above the normal boiling points of any solvents employed may be achieved by resort to superatmospheric pressures, in accord with standard practices.

REACTION TIMES

The minimum contact time required to attain a desired yield of product under any given set of conditions is readily determined by a few laboratory tests. In general, reaction times of from about 4 to about 24 hours at temperatures of from about 120° to about 75° will be found sufficient for the attainment of satisfactory yields.

REACTANT RATIOS

At least one molecular proportion of hydrazine is required for each molecular proportion of the tetrahalopyridyl alkyl sulfide to be reacted. Hydrogen chloride is a product of the reaction and will form a hydrochloride with any hydrazine base present, unless a hydrogen chloride acceptor, such as — for example — an alkali or alkaline earth metal oxide, hydroxide or carbonate or a tertiary amine, is also present. If desired, an excess of hydrazine, hydrazine hydrate or a hydrazine salt of an acid weaker than hydrogen chloride may be employed as the acid acceptor. In the latter case, a hydrazine to tetrahalo-4-alkylthiopyridine mole ratio of about 2.2/1 appears to be optimal.

A preferred embodiment of the present method comprises maintaining a solution of one molecular proportion of a tetrahalo-4-alkylthiopyridine, as above defined, and from about 1.3 to about 1.7 molecular proportion of hydrazine or hydrazine hydrate, in a polar organic solvent containing not more than about 20 wt. % of water, at a temperature of from about 85° to about 110°C. for a period of from about 8 to about 16 hours, in the presence of at least one equivalent proportion of a hydrogen chloride acceptor.

II. Oxidative conversion of a 6-hydrazino-2,3,5-trichloro-4-alkylthiopyridine to the corresponding 6-H compound

OXIDANTS

Any otherwise suitable oxidant capable of effecting oxidation of the hydrazino moiety may be employed in the oxidation step. Exemplary of such oxidants are aqueous hydrogen peroxide, air, aqueous cupric sulfate, silver oxide in ethanol or aprotic media and aqueous alkali or alkaline earth metal hypochlorites or hypobromites. Alkali metal hypochlorites are preferred. Commercial, base stabilized, chlorine bleach solutions are a convenient source of hypochlorite for the oxidation.

Hydrazine, conveniently as the hydrate, may itself be employed as the oxidant. Although aqueous sodium hydroxide is a known oxidant for pyridyl hydrazines, this is not a preferred oxidant in the present method, since hydrolysis of a 2- (or 6) halogen substituent may result to some extent.

pH

The oxidation may be carried out at pH's ranging from about 3 to 14, depending somewhat on the particular type of oxidant employed. In general, however, pH's in excess of 7 are preferred. When the oxidation is carried out on the acid side, as with air and a copper salt or with hydrogen peroxide/$H_2SO_4$, yields of the trihalopyridyl alkyl sulfide are relatively poor and colored by-products tend to form. In certain instances, it may be desirable to add a base, such as sodium hydroxide as the reaction progresses. For example, the decomposition of hydrogen peroxide is accelerated by bases, but if the hydrazino compound is mixed with hydrogen peroxide first and the pH then carefully adjusted above neutral with sodium hydroxide, this does not present a serious problem. As a further example, sulfuric acid is formed when cupric sulfate is employed as the oxidant, according to the following equation:

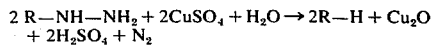

and the addition of at least four equivalents of base will be required to keep the reaction mixture on the basic side.

A pH range of about 11 to 14 is preferred for most oxidants, and particularly so when a hypohalite or the combination of air with a cupric salt catalyst — such as cupric chloride or cupric sulfate, for example — is used.

OXIDATION TEMPERATURE

Temperature is not a highly critical parameter of the oxidation step, but for any given hydrazino compound, the highest temperature which can be used without excessive side reactions or decomposition occurring will be preferable. In general, temperatures within the range of about 25°–150° are suitable.

The reflux temperature of the medium employed will generally be a convenient temperature, adjustable up or down by corresponding pressure adjustments. Since aqueous media and atmospheric pressure are generally preferred, a temperature range of about 80°–100° will frequently be employed. If a hypohalite is used as the oxidant, temperatures of from about 90° to about 100° are preferred.

OXIDATION TIMES

Suitable oxidation times generally range from about 0.25 to about 24 hours, depending somewhat upon the particular oxidant/medium combination selected and on the reaction temperature employed. The minimum time required to attain a given degree of conversion of the hydrazino compound under any particular set of conditions can readily be determined by a few laboratory scale oxidations. In general, however, a reaction time of from about ½ to about 4 hours will be sufficient.

III. Oxidation of the alkylsulfide moiety in situ after oxidation of the hydrazino group When the trihalopyridyl alkyl sulfide is to be prepared (from the hydrazino compound) as a precursor to the corresponding sulfoxide or sulfone, it is economically advantageous to oxidize the sulfide group in situ, without isolating the trihalopyridyl alkyl sulfide. In general, oxidation of the sulfide group — particularly to a sulfone — will require a stronger oxidant and/or more rigorous conditions than oxidation of the hydrazino moiety. Consequently, the oxidants and conditions known (U.S. Pat. Nos. 3,296,272 and 3,415,832) to be suitable for the oxidation of polyhalopyridyl alkyl sulfides to sulfoxides and/or sulfones will also be generally suitable for oxidative replacement of a 2- (or 6) hydrazino substituent by a hydrogen. However, whereas the initial oxidation (of the hydrazino group) is ordinarily carried out on the basic side, oxidation of the sulfide group usually requires acid conditions. Accordingly, the first oxidation will generally be carried out at a pH above 7 and the second oxidation at a pH below 7.

Since an aqueous medium is generally used for the initial oxidation, it will usually be necessary to select an oxidant for the second step which can also be employed in water, if the advantage of in situ operation is to be realized. Chlorine/water is particularly advantageous in this regard. That is, chlorine is passed into a solution or suspension of the hydrazino compound in an aqueous base to form the hypohalite, as needed, for the initial oxidation, the amount of base being regulated so that continued chlorine addition will result in the pH shift desired for the second oxidation, after the amount of chlorine required for the first oxidation has been consumed.

In the method of the present invention wherein a 2,3,5-trihalo-6-hydrazino-4-alkylthio pyridine is formed as the first step in a sequence of two steps, the second step being oxidation of the hydrazino group, said second step is preferably carried out by contacting one molecular proportion of the hydrazino compound with at least one equivalent of an oxidant at a pH greater than about 7 in an aqueous medium. The latter oxidant preferably is hypochlorite ion, which is conveniently provided under acid conditions by the reaction of molecular chlorine with water:

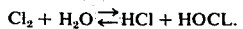

A particularly preferred embodiment of the present process invention is one in which a 2,3,5-trihalo-6-hydrazino-4-alkylthiopyridine is formed as the first step in a sequence of three steps, the second step being oxidation of the hydrazino group and the third step being oxidation of the 4-alkylthio group to a 4-alkylsulfinyl- or 4-alkylsulfonyl group. In the most preferred version of this embodiment, hypochlorite is employed, at a pH greater than 7, as the oxidant in the second step and, at a pH less than 7, as the oxidant in the third step, which is carried out in situ.

If both oxidations are to be carried out simultaneously, or at least in a single operation, a pH of from about 6.5 to about 7.5 is indicated by the foregoing considerations.

IV. Isolation and oxidation of the trihalo-4-alkylthiopyridine

If desired, the third step (the second oxidation step) in the three-step embodiment of the present process invention may be carried out in a known manner. That is, the alkylthiopyridine compound produced in the second step is isolated and then oxidized, as — for example — in acetic acid solution with hydrogen peroxide or in aqueous suspension with chlorine.

SPECIFIC EMBODIMENTS

EXAMPLE 1

Synthesis of
3,5,6-Trichloro-2-Hydrazino-4-(n-propylthio)-pyridine by displacement of a chlorine with a hydrazino group Into a three-neck 12-liter round bottom flask, equipped with mechanical stirrer, cooling condenser and heating mantle, was added 645 g. (2.216 moles) of 2,3,5,6-tetrachloro-4-(n-propylthio)-pyridine, 5.5 liters of isopropyl alcohol and 279 g. (5.58 moles) of 100% hydrazine hydrate. The reaction mixture was refluxed for 16 hours, cooled to ~18°C. and the solid product was filtered out. After a thorough washing with water, the solid was dried for 12 hours under vacuum at ~40°C. The yield of trichloro-2-hydrazino-4-(n-propylthio)-pyridine (melting point 117°–9°C.) was 520.6 g. or 80.3% of theory.

EXAMPLE 2

Synthesis of
2,3,5-Trichloro-4-(n-propylsulfonyl)-pyridine by oxidation of the hydrazino and propyl thio groups Into a 1-liter, baffled resin pot, equipped with mechanical stirrer, cooling condenser and heating mantle, was weighed 20 g. (0.07 mole) of 3,5,6-trichloro-2-hydrazino-4-(n-propylthio)-pyridine, 1.5 g. of Emersal surfactant, 0.3 g. of Dow-Corning Antifoam A, and 350 g. of water. The pH was adjusted to 11 with 50% aqueous sodium hydroxide. The slurry was heated to 90°C. and 100 ml. of 2N aqueous hypochlorite bleach was added over a 60-minute period, followed by 27 minutes of additional stirring. The two-phase liquid system was cooled to ~30°C. and chlorine gas was sparged into it with good stirring. After the initial exotherm to ~40°C., the sparging of chlorine was continued for 3 hours at 50°C. 2,3,5-Trichloro-4-(n-propylsulfonyl)-pyridine was filtered out, washed with water and dried under vacuum at ~40°C.; m.p. 81°–2°C. The yield was 18.5 g. or 92.0% of theoretical and the purity was 96.6% as determined by glc analysis.

EXAMPLE 3

Reaction of Tetrachloro-4-(n-propylthio) pyridine with $NH_2NH_2/NaHCO_3$ and oxidation of product Into a 500 ml. round-bottom flask were weighed:
20 g. of tetrachloro-4-(n-propylthio)pyridine
170 ml. of isopropyl alcohol
3.41 g. of $NH_2NH_2.H_2O$, and
8.6 g. of $NaHCO_3$.

The mixture was refluxed for 20 hours, cooled and the alcohol distilled off under aspirator vacuum, with a simultaneous addition of water. After adding about 290 ml. of $H_2O$ all the alcohol was removed from the system. The pH was adjusted to 12.8 with 50% NaOH and Emersal (~2 g.) and Antifoam A (~1 g.) added to the white slurry. It was heated to 100°. All the solid melted. The temperature was lowered to ~90°C. and there was added 38 ml. of 3.96 N aqueous hypochlorite bleach over 30-minute period. The resultant slurry was heated another 30 minutes at 90°C. and cooled. Thin layer chromatography indicated that all the hydrazino compound was oxidized. It was left overnight at room temperature.

The slurry turned coffee-brown overnight. Chlorine was sparged into the stirred slurry. The slurry lightened considerably and the temperature rose to ~30°. There was added ~1 g. Emersal and the chlorine flow and stirrer were speeded up. After ~30 min. the product was a light beige solid. Heating was started after 1½ hours at 30°C., after which the mixture was stirred 2½ hours at 50°C. After cooling to 45°C., the mixture was added to 1.5 liters of $H_2O$ containing ~10 g. of $NaHCO_3$. The beige solid was filtered out and dried under vacuum at 38°C.; 17.4 g.; m.p. 76°–82°C. The product analyzed by TLC and glc as containing 85% of the desired trichloro sulfone product and 15% tetrachloro-4-n-propyl sulfonyl pyridine. Each of the latter sulfones are active fungicides and may be employed as the mixed product.

EXAMPLE 4

Three-Step Process for Production of
2,3,5-Trichloro-4-(n-propylsulfonyl)-Pyridine

Step 1

Into a 1 liter Parr bomb, equipped with a glass liner, a tantalum-metal stirrer and a nitrogen inlet tube was measured:
40.0 g. (0.137 mole) of tetrachloro-4-(n-propylthio)-pyridine,
340 ml. of methanol
8.9 g. (0.178 mole) of hydrazine hydrate, and
17.2 g. (0.204 mole) of sodium bicarbonate.

The bomb was heated for 10 hours at 100°C. under a pressure of 60 psig with a slow $N_2$ gas sweep through the system. After cooling the reaction mixture, it was transferred into a one liter resin bottle, equipped with a distillation condenser, mechanical stirrer, thermometer, heating mantle and an additional funnel. The system was placed under aspirator vacuum and methanol distilled from the system with simultaneous addition of water. A total of about 700 ml. of water was added and enough was distilled from the system so that the final volume of water in the resin kettle was about 350 ml.

Step 2

The pH of the aqueous slurry was adjusted to about 13 with 50% aqueous NaOH and about 2 g. of Emersal surfactant and about 1 g. of Dow-Corning Antifoam Compound A were added. Heated to about 90°C. and added 190 ml. of 3.26 N aqueous sodium hypochlorite (bleach) over a 60-minute period. After another 30 minutes of heating, the two phase system was cooled to room temperature.

Step 3

Chlorine was sparged into the reaction and the temperature rose to about 40°C. After the exotherm, the sparging of chlorine was continued and the reaction mixture heated to 55°C. for 3 hours. The mixture was cooled to room temperature, and filtered. The solid filtrand was washed thoroughly with water. The yield was 29.8 g. or 75.1%; m.p. 73°-8°C. Purity by glc: 85.9% of the title sulfone.

EXAMPLE 5

Oxidation of 6-hydrazino-4-n-propylthio-2,3,5-trichloropyridine (I) in methanol with air A 5 gram sample of (I) was dissolved in 300 ml. of reagent methanol and air was sparged into the solution for 2.5 hrs. The progress of the oxidation was followed by developing samples of the reaction mixture by TLC. After 2.5 hrs. no starting material could be detected and the methanol was removed in vacuo and the residue extracted with equal parts of $H_2O/CH_2Cl_2$. The organic layer was dried with $Na_2SO_4$ and evaporated to dryness yielding 4.1 g. of 4-(n-propylthio)-2,3,5-trichloropyridine. G.C. analysis with an internal standard showed the material to be 97% pure.

EXAMPLE 6

Air oxidation of 6-hydrazino-2,3,5-trichloro-4-(n-propyl) thiopyridine in water, with and without catalyst Ten g. of the 6-hydrazino compound was slurried in 200 ml. of $H_2O$ with 1 g. of Emersal and 0.12 g. of $CuCl_2.H_2O$. The pH was adjusted to 12 with addition of caustic and the temperature was brought to 90°C. Air was sparged in at the rate of 2 lit/min. for 8 hrs. The trichloropropyl sulfide product was extracted from the aqueous emulsion with 200 ml. of distilled hexane. After the hexane was removed by vacuum, 8.48 g. of dark colored trichloro-4-(n-propyl)thiopyridine product remained (94.7% pure by TLC).

At room temperature, a 5% slurry of the trichloro-6-hydrazino-4-(n-propyl)thio compound in water was oxidized by air to the extent of only 11% after a 12-hr. period but copper salts were found to be effective catalysts for aqueous oxidation using either air or pure oxygen. Under the proper conditions, good yields of the trichloro propyl sulfide could be obtained from aqueous oxidations using $CuCl_2$ catalyst and heat.

Reaction variables:

| Time | Oxidant | Temp. | pH | Catalyst Amount | Trichloro Product Yield |
| --- | --- | --- | --- | --- | --- |
| 1.5 hrs. | $O_2$ | 85° | 10 | 20 mole % | 84% |
| 17.5 hrs. | $O_2$ | 85° | 10 | 2 mole % | 79% |
| 2.5 hrs. | $O_2$ | 85° | 7 | 0.2 mole % | 86% |
| 8 hrs. | Air | 70° | 3 | 0.2 mole % | 13.84% |
| " | " | " | 9 | 0.2 mole % | 46.4% |
| " | " | " | 11 | " | 76.7% |
| " | " | " | 12 | " | 83.6% |
| " | " | 90° | 12 | " | 94.7% |

The 6-hydrazino-2,3,5-trihalo-4-alkylthio pyridines of the present invention are fungicidal in their own right and are generally active as microbicides and industrial preservatives. They can be applied to the aerial portions of growing plants to control leaf-attacking fungal organisms or dispersed in soil or applied to plant seeds to control the root and seed attacking organisms of mold and damping off. In still other operations they can be applied to orchard floor surfaces to control over-wintering spores of various fungal organisms. In still further operations, the compounds of the present invention or compositions containing them as active constituents can be included in and on plaster, ink, wallboard, textiles, paper, adhesives, soaps, synthetic detergents, cutting oils, polymeric materials, embalming fluids, oil paints and latex paints to prevent the attack of various fungal pests and the subsequent economic loss due to the degradation of such products from the attack of the organisms of rot, mold and decay.

In such applications, the effective concentration of the toxicant may vary considerably. In liquid compositions the required dosage will generally be within the range of from about 0.001 to 50 percent by weight. In dusts, concentrations of from about 0.1 to 95 percent by weight may be employed, according to conventional formulation and application practices. The compounds may conveniently be employed as wettable powders for foliar sprays or seed treatments.

EXAMPLE 7

In a representative operation, 6-hydrazino-2,3,5-trichloro-4-(n-propylthio)-pyridine was tested as the sole toxicant in each of a number of nutrient agars innoculated with different microorganisms, as listed below, with the results shown.

| Organism | Toxicant Concentration | Organism Inhibited | Killed |
| --- | --- | --- | --- |
| Staphylococcus aureus | 10 ppm | X | — |
|  | 100 ppm | X | X |
| Tricophton mentagrophytes | 500 ppm | X | X |
| Bacillus subtilis | 500 ppm | X | X |
| Mycobacterium phlei | 10 ppm | X | X |
| Rhizopus nigricans | 500 ppm | X | X |
| Trichoderm sp. Madison P-42 | 500 ppm | X | X |

In another representative operation, the test compound was also found to give 95% control of Apple Scab fungus when applied, at a concentration of 100 ppm, to host plants innoculated with the fungus and maintained under appropriate conditions of humidity and temperature until disease symptoms on control plants were well established.

In further representative operations, each of the following 6-hydrazino compounds are prepared as taught earlier herein and tested in nutrient agars as above, and are found effective at a concentration of 500 ppm to at least inhibit (give 50% control of) at least one of the organisms listed below:

Organisms

Staphylococcus aureus
Escherichia coli
Candida albicans
Trichophton mentagrophytes
Aspergillus Niger
Bacillus subtilis
Aerobacter aerogenes
Candida pelliculosa
Pullularia pullulans
Salmonella typhosa
Pseudomonas sp. strain 10
Mycobacterium phlei
Rhizopus ingricans
Ceratocystis ips
Trichoderm sp. Madison P-42

6-Hydrazino-2,3,5-trichloro-4-(alkylthio) pyridines preparable from 2,3,5,6-tetrachloro- or 2-bromo-3,5,6-trichloro-4-(alkylthio) pyridines by reaction with hydrazine:

| Alkyl Group | Emperical Formula of Compound | Molecular Weight |
|---|---|---|
| Methyl | $C_6H_6Cl_3N_3S$ | 258.58 |
| Ethyl | $C_7H_8Cl_3N_3S$ | 271.60 |
| Isopropyl | $C_8H_{10}Cl_3N_3S$ | 284.62 |
| Isobutyl | $C_9H_{12}Cl_3N_3S$ | 297.64 |
| 1-pentyl | $C_{10}H_{14}Cl_3N_3S$ | 310.66 |

6-Hydrazino-2-bromo-3,5-dichloro-4-(alkylthio) pyridines preparable from 2,6-dibromo-3,5-dichloro-4-(alkylthio)-pyridines by reaction with hydrazine:

| Alkyl Group | Empirical Formula | Molecular Weight |
|---|---|---|
| Methyl | $C_6H_6BrCl_2N_3S$ | 303.04 |
| Ethyl | $C_7H_8BrCl_2N_3S$ | 316.06 |
| n-Propyl | $C_8H_{10}BrCl_2N_3S$ | 329.08 |
| Sec-Butyl | $C_9H_{12}BrCl_2N_3S$ | 342.10 |
| 2-Methyl-3-Butyl | $C_{10}H_{14}BrCl_2N_3S$ | 355.12 |

6-Hydrazino-2,3,5-tribromo-4-(alkylthio)pyridines preparable from 2,3,5,6-tetrabromo-4-(alkylthio)pyridines by reaction with hydrazine:

| Alkyl Group | Emperical Formula | Molecular Weight |
|---|---|---|
| Methyl | $C_6H_6Br_3N_3S$ | 391.96 |
| Ethyl | $C_7H_8Br_3N_3S$ | 404.98 |
| n-Propyl | $C_8H_{10}Br_3N_3S$ | 418.00 |
| t-Butyl | $C_9H_{12}Br_3N_3S$ | 431.02 |
| 2-Pentyl | $C_{10}H_{14}Br_3N_3S$ | 444.04 |
| Neopentyl | $C_{10}H_{14}Br_3N_3S$ | 444.04 |

We claim:
1. A process for preparing a hydrazino-trihaloalkylthiopyridine of the formula

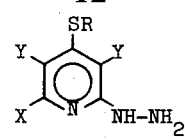

wherein R is an alkyl group of from 1 to 5 carbons; X is Cl or Br; and Y, which is the same in each occurrence, is Cl or Br, except that Y cannot be Br when X is Cl;

comprising reacting with hydrazine the corresponding tetrahalo-4-(alkylthio)pyridine of the formula

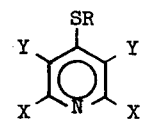

wherein R, X and Y are as above defined, thereby effecting replacement of one X in said tetrahalo-4-(alkylthio)pyridine with an —NH—NH$_2$ moiety.

2. The process of claim 1 additionally comprising reacting the resulting 6-hydrazino compound with an oxidant, thereby effecting replacement of the hydrazino moiety with a hydrogen.

3. The process of claim 2 in which said oxidant is employed under basic conditions.

4. The process of claim 2 in which the oxidant is hypochlorite or hypobromite ion.

5. The process of claim 2 additionally comprising reacting the resulting trihalo-4-(alkylthio)pyridine with an oxidant, thereby converting the alkylthio group to an alkylsulfinyl or alkylsulfonyl group.

6. The process of claim 5 wherein hypochlorite or hypobromite ion is employed as an oxidant at a pH above 7 to effect replacement of the hydrazino moiety and at a pH below 7 to effect oxidation of the alkylthio group.

* * * * *